US00PP14789P2

(12) United States Plant Patent
Saul

(10) Patent No.: US PP14,789 P2
(45) Date of Patent: May 18, 2004

(54) ALTERNANTHERA PLANT NAMED 'PARTYTIME'

(50) Latin Name: *Alternanthera ficoidea*
Varietal Denomination: Partytime

(76) Inventor: Robert Mark Saul, 940 Carter Dr., Atlanta, GA (US) 30319

( * ) Notice: Subject to any disclaimer, the term of this patent is extended or adjusted under 35 U.S.C. 154(b) by 0 days.

(21) Appl. No.: 10/313,153

(22) Filed: Dec. 6, 2002

(51) Int. Cl.[7] ..... A01H 5/00
(52) U.S. Cl. ..... Plt./373
(58) Field of Search ..... Plt./373

*Primary Examiner*—Kent Bell
*Assistant Examiner*—Louanne Krawczewicz Myers
(74) *Attorney, Agent, or Firm*—C. A. Whealy

(57) ABSTRACT

A distinct cultivar of Alternanthera plant named 'Partytime', characterized by its upright and rounded plant habit; freely branching habit; bushy and dense growth habit; and green, creamy white and red purple-colored leaves.

1 Drawing Sheet

Botanical classification/cultivar designation: *Alternanthera ficoidea* cultivar Partytime.

BACKGROUND OF THE INVENTION

The present Invention relates to a new and distinct cultivar of Alternanthera plant, botanically known as *Alternanthera ficoidea,* and hereinafter referred to by the cultivar name Partytime.

The new Alternanthera was discovered in June, 2000, by the Inventor in a controlled environment in Atlanta, Ga., as a naturally-occurring branch mutation of an unidentified selection of *Alternanthera ficoidea,* not patented. The cultivar Partytime was selected by the Inventor on the basis of its unique foliage coloration.

Asexual reproduction of the new cultivar by vegetative cuttings taken in Atlanta, Ga., since August, 2000, has shown that the unique features of this new Alternanthera are stable and reproduced true to type in successive generations.

SUMMARY OF THE INVENTION

Plants of the cultivar Partytime have not been observed under all possible environmental conditions. The phenotype may vary somewhat with variations in environment such as temperature and light intensity without, however, any variance in genotype.

The following traits have been repeatedly observed and are determined to be the unique characteristics of 'Partytime'. These characteristics in combination distinguish 'Partytime' as a new and distinct cultivar:

1. Upright and rounded plant habit.
2. Freely branching habit; bushy and dense growth habit.
3. Green, creamy white and red purple-colored leaves.

Plants of the new Alternanthera differ from plants of the parent selection primarily in foliage coloration as plants of the parent selection had green and burgundy-colored foliage. Plants of the new Alternanthera differ primarily from plants of known cultivars of *Alternanthera ficoidea* in leaf coloration.

BRIEF DESCRIPTION OF THE PHOTOGRAPHS

The accompanying colored photographs illustrate the unique appearance of the new cultivar, showing the colors as true as it is reasonably possible to obtain in colored reproductions of this type. Colors in the photographs may differ from the color values cited in the detailed botanical description which accurately describe the colors of the new Alternanthera.

The photograph at the top of the sheet is a close-up view of a typical plant of 'Partytime'.

The photograph at the bottom of the sheet comprises a close-up view of typical leaves of a plant of 'Partytime'.

DETAILED BOTANICAL DESCRIPTION

In the following description, color references are made to The Royal Horticultural Society Colour Chart, 1995 Edition, except where general terms of ordinary dictionary significance are used. Plants used in the aforementioned photographs and in the following description were grown in Atlanta, Ga. in one-gallon containers in a polyethylene-covered greenhouse and under conditions which closely approximate commercial production conditions. In the greenhouse, day temperatures ranged from 75 to 85° F. and night temperatures ranged from 60 to 75° F. Plants were about six months old when the photographs and description were taken. The photographs and description were taken during the early summer.

Botanical classification: *Alternanthera ficoidea* cultivar Partytime.

Parentage: Naturally-occurring branch mutation of an unidentified *Alternanthera ficoidea* selection, not patented.

Propagation:
- *Type cutting.*—By vegetative cuttings.
- *Time to initiate roots.*—About 7 days at 75° F.
- *Time to produce a rooted cutting or liner.*—About 21 days at 75° F.
- *Root description.*—Fine.
- *Rooting habit.*—Freely branching.

Plant description:
- *Form/growth habit.*—Upright and rounded plant habit; vigorous.

*Plant height, soil level to top of plant plane.*—About 37 cm.

*Plant diameter or area of spread.*—About 35 cm.

*Branching habit.*—Freely branching with lateral branches forming at potential every node; pinching enhances lateral branch formation; dense and bushy growth habit.

*Lateral branches.*—Length: About 32 cm. Diameter: About 3.5 mm. Internode length: About 3 mm. Texture: Smooth, glabrous. Color: 146A overlain with close to 59A.

*Foliage description.*—Arrangement: Opposite, simple. Length: About 5.5 cm. Width: About 3.75 cm. Shape: Ovate. Apex: Acute. Base: Obtuse. Margin: Entire. Texture, upper and lower surfaces: Slightly pubescent. Venation pattern: Pinnate. Color: Young and fully expanded foliage, upper surface: Random and irregular areas of green, more green than 146A; red purple, 57A; and creamy white, close to 158A. Young and fully expanded foliage, lower surface: Random and irregular areas of green, close to 146C; red purple, close to 58A; and creamy white, close to 158A. Venation, upper and lower surfaces: Same as lamina. Petiole: Length: About 1.5 cm. Diameter: About 1 mm. Texture, upper and lower surfaces: Pubescent. Color: Upper surface: 57A. Lower surface: Close to 58A to 58B.

Flower description: Flower development has not been observed on plants of the new Alternanthera.

Disease/pest resistance: Under commercial production conditions, plants of the new Alternanthera have not been observed to be resistant to pathogens or pests common to Alternanthera.

Weather tolerance: Plants of the new Alternanthera have been shown to be tolerant to rain, wind and to temperatures ranging from 32 to more than 100° F.

It is claimed:

1. A new and distinct cultivar of Alternanthera plant named 'Partytime', as illustrated and described.

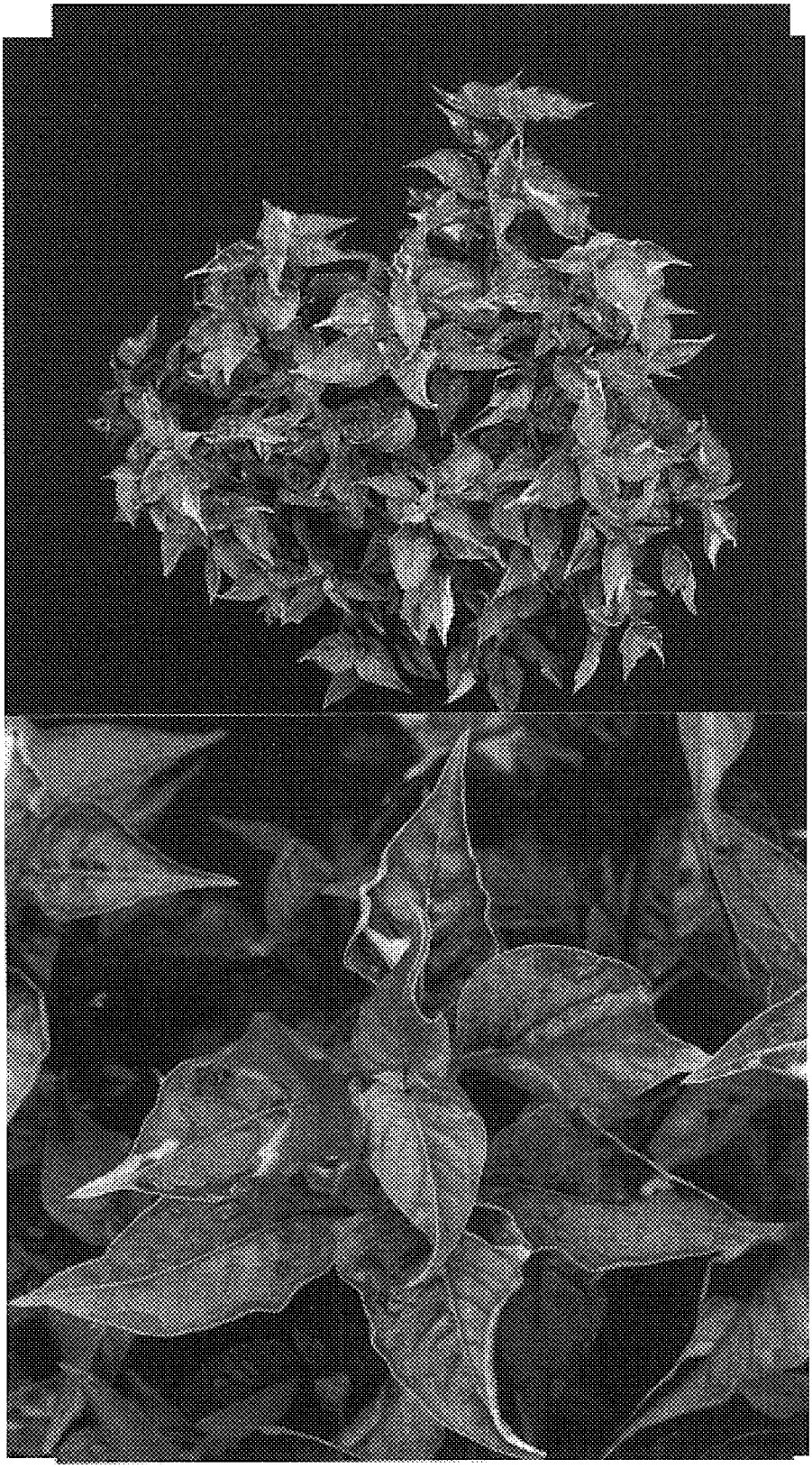

* * * * *